United States Patent [19]
Campbell et al.

[11] Patent Number: 5,800,494
[45] Date of Patent: Sep. 1, 1998

[54] MICROWAVE ABLATION CATHETERS HAVING ANTENNAS WITH DISTAL FIRE CAPABILITIES

[75] Inventors: Thomas H. Campbell, San Carlos; Peter Sturzu, Cupertino, both of Calif.

[73] Assignee: Fidus Medical Technology Corporation, Fremont, Calif.

[21] Appl. No.: 700,291

[22] Filed: Aug. 20, 1996

[51] Int. Cl.$^6$ .................................. A61N 1/00
[52] U.S. Cl. .................. 607/116; 607/100; 607/101; 607/155; 607/156; 606/33
[58] Field of Search ................ 606/33; 607/99, 607/100, 101, 102, 116, 154, 155, 156, 11

[56] References Cited

U.S. PATENT DOCUMENTS

| | | | |
|---|---|---|---|
| 4,409,993 | 10/1983 | Furihata | 128/784 |
| 4,583,556 | 4/1986 | Hines et al. | 607/154 |
| 4,601,296 | 7/1986 | Yerushalmi | 128/804 |
| 4,800,899 | 1/1989 | Elliott | 128/804 |
| 4,841,988 | 6/1989 | Fetter et al. | 128/804 |
| 4,945,912 | 8/1990 | Langberg | 128/642 |
| 5,097,845 | 3/1992 | Fetter et al. | 128/804 |
| 5,129,396 | 7/1992 | Rosen et al. | 128/653.1 |
| 5,190,054 | 3/1993 | Fetter et al. | 128/804 |
| 5,230,349 | 7/1993 | Langberg | 128/786 |
| 5,246,438 | 9/1993 | Langberg | 606/33 |
| 5,314,466 | 5/1994 | Stern et al. | 607/156 |
| 5,364,336 | 11/1994 | Carr | 600/2 |
| 5,370,644 | 12/1994 | Langberg | 606/33 |
| 5,370,677 | 12/1994 | Rudie et al. | 607/101 |
| 5,370,678 | 12/1994 | Edwards et al. | 607/101 |
| 5,383,922 | 1/1995 | Zipes et al. | 607/122 |
| 5,405,346 | 4/1995 | Grundy et al. | 606/41 |

*Primary Examiner*—Jennifer Bahr
*Assistant Examiner*—David M. Ruddy
*Attorney, Agent, or Firm*—Hickman Beyer & Weaver, LLP

[57] ABSTRACT

A variety of improved antenna arrangements for ablation catheters and methods for constructing catheter with these antenna arrangements are described. In various apparatus aspects of the invention, the catheter includes an elongated flexible tubular member adapted to be inserted into a vessel in the body of a patient. A transmission line suitable for transmitting electromagnetic energy is received within the tubular member. An antenna is coupled to the transmission line for generating an electric field sufficiently strong to cause tissue ablation. In one embodiment, the antenna takes the form of an antenna coil that is oriented such that its longitudinal axis extends substantially perpendicular to the longitudinal axis of the flexible tubular member. In another embodiment, a plurality of such laterally oriented antenna coils are provided at longitudinally spaced locations relative to the catheter axis. In other embodiments, the antenna coil is spirally wound. A variety of spiral antenna arrangements are contemplated. In some embodiments, the coil is wound in a substantially conical or frusto-conical manner expanding either distally or proximately. In still another embodiment, the antenna coil is wound in a substantially flat coil.

34 Claims, 10 Drawing Sheets

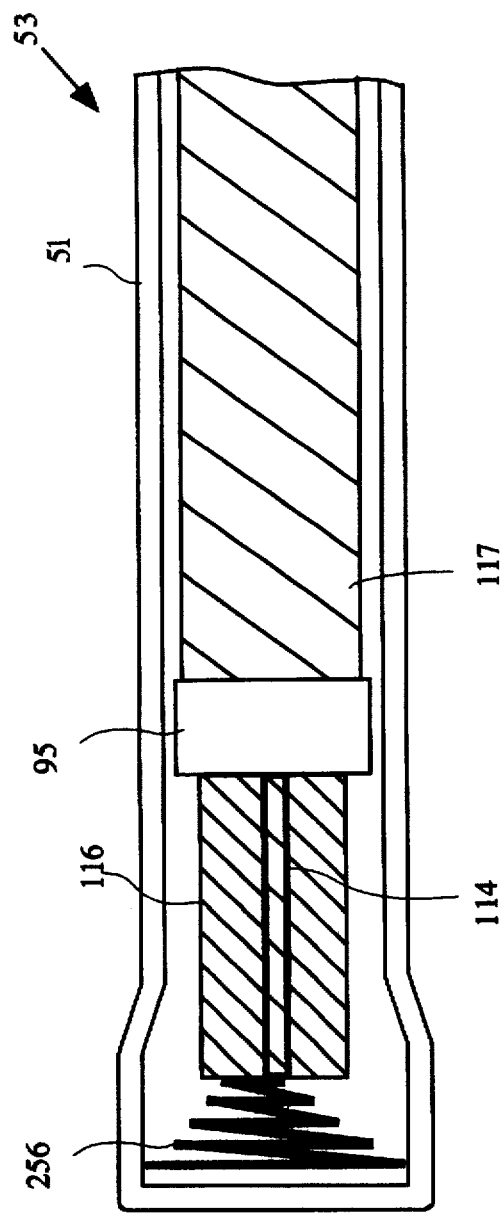
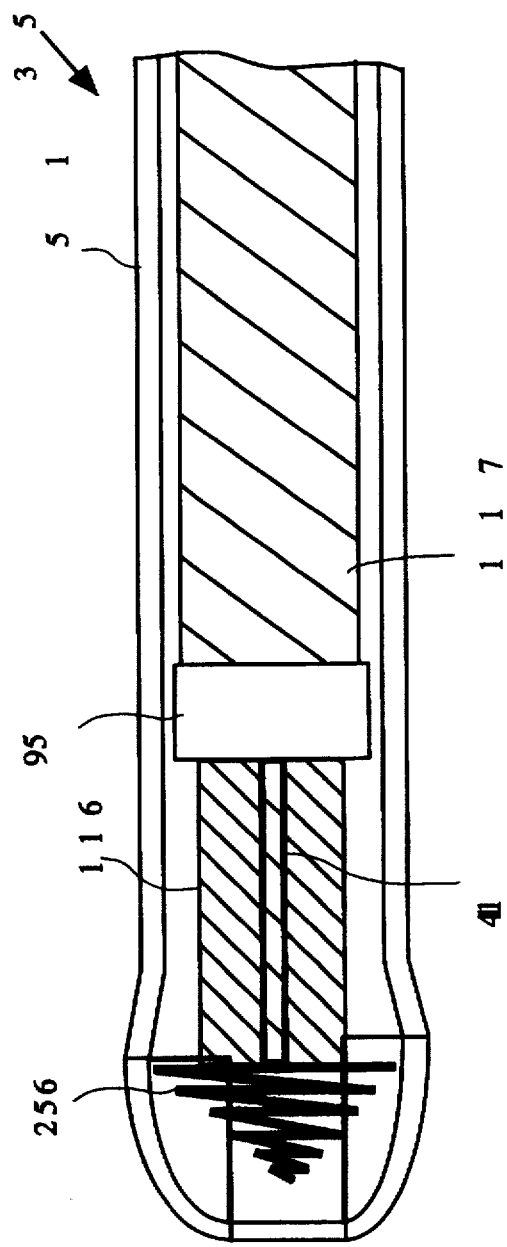

MICROWAVE ABLATION CATHETERS HAVING ANTENNAS WITH DISTAL FIRE CAPABILITIES

BACKGROUND OF THE INVENTION

The present invention relates generally to ablation catheter systems that use electromagnetic energy in the microwave frequencies to ablate internal bodily tissues. More particularly, a variety of antenna arrangements and catheter construction techniques are disclosed that direct the microwave energy in generally distal directions including general forward directions and in directions that are relatively closely contained along the antenna.

Catheter ablation has recently become an important therapy for certain cardiac arrhythmias, cardiac disrhythmias and tachycardia. Most approved ablation catheter systems now utilize radio frequency (RF) energy as the ablating energy source. Accordingly, a variety of RF based catheters and power supplies are currently available to electrophysiologists. However, radio frequency energy has several limitations including the rapid dissipation of energy in surface tissues resulting in shallow "burns" and failure to access deeper arrhythmic tissues. Another limitation of RF ablation catheters is the risk of clot formation on the energy emitting electrodes. Such clots have an associated danger of causing potentially lethal strokes in the event that a clot is dislodged from the catheter.

A second common ablation approach is the use of high voltage, direct current defibrillator discharges. Direct current ablation has several drawbacks including the need for general anesthesia and explosive discharges that can cause debris or even rupture certain cardiac organs. For these and other reasons, significant attention has been given recently to alternative ablative energy sources.

Microwave frequency energy has long been recognized as an effective energy source for heating biological tissues and has seen use in such hyperthermia applications as cancer treatment and preheating of blood prior to infusions. Accordingly, in view of the drawbacks of the traditional catheter ablation techniques, there has recently been a great deal of interest in using microwave energy as an ablation energy source. The advantage of microwave energy is that it is much easier to control and safer than direct current applications and it is capable of generating substantially larger lesions than RF catheters, which greatly simplifies the actual ablation procedures. Accordingly, there are a number of catheters under development which utilize electromagnetic energy in the microwave frequency range as the ablation energy source. By way of example, such systems are described in the U.S. Pat. Nos. 4,641,649 to Walinsky; 5,246,438 to Langberg; 5,405,346 to Grundy, et al.; and 5,314,466 to Stern, et al, each of which is incorporated herein by reference.

Most of the existing microwave ablation catheter contemplate the use of longitudinally extending helical antenna coils that direct the electromagnetic energy in a direction that is generally perpendicular to the longitudinal axis of the catheter although the fields created are not well constrained to the antenna itself. Although such catheter designs work well for a number of applications, it would also be desirable to provide microwave ablation catheter designs that are capable of effectively transmitting electromagnetic energy in other specific directions, such as a generally forward direction relative to the longitudinal axis of the catheter. In other applications, it would be desirable to transmit electromagnetic energy in a direction perpendicular to the longitudinal axis of the catheter, but to constrain the energy to a region that more closely approximates the length of the antenna.

SUMMARY OF THE INVENTION

To achieve the foregoing and other objects and in accordance with the purpose of the present invention, a variety of improved ablation catheters and particularly microwave ablation catheters are disclosed. In some embodiments, antennas suitable for generating an electric field having a significant forward component are described. In other embodiments, antennas having improved characteristics in a direction perpendicular to the antenna are disclosed. In various apparatus aspects of the invention, the catheter includes an elongated flexible tubular member adapted to be inserted into a vessel in the body of a patient. A microwave transmission line suitable for transmitting electromagnetic energy is received within the tubular member. An antenna is coupled to the transmission line for generating an electric field sufficiently strong to cause tissue ablation.

In one embodiment, the antenna takes the form of an antenna coil that is oriented such that its longitudinal axis extends substantially perpendicular to the longitudinal axis of the flexible tubular member. In one preferred embodiment, the antenna coil has at least two full turns. In another, the antenna coil has in the range of two to four full turns. In some embodiments the antenna coil is coupled directly to the center conductor of a coaxial cable that forms the microwave transmission line. In others the antenna coil is an extension of the center conductor.

In another embodiment, a plurality of the laterally oriented antenna coils are provided at longitudinally spaced locations relative to the catheter axis. In one such embodiment, these spaced antenna coils are formed from a single wire.

In other embodiments of the invention, the antenna coil is spirally wound. A variety of spiral antenna arrangements are contemplated. In some embodiments, the coil is wound in a substantially conical or frusto-conical manner. In one embodiment the antenna coil expands distally such that a distal end of the antenna coil has a larger diameter than a proximal end of the antenna coil. In another, the antenna coil contracts distally such that a distal end of the antenna coil has a smaller diameter than a proximal end of the antenna coil. In still another embodiment, the antenna coil is wound in a substantially flat coil.

In still other embodiments, one end of the antenna coil is grounded to the shield, as for example, by soldering the coil directly to the shield. In one such preferred embodiment, a longitudinally extending helical coil is provided. The distal end of the coil is attached to or an extension of the center conductor of a coaxial cable that forms the microwave transmission line. The proximal end of the coil is attached to the shield of the coax cable.

In some embodiments, it may be desirable to provide ECG electrodes for mapping and monitoring. The electrodes may include a distal mapping electrode, one or more lateral mapping electrodes (which may be rings), and/or one or more lateral mapping electrode bands that each include a plurality of isolated electrodes. In some embodiments, one or more of the lateral mapping electrodes may be positioned adjacent the antenna coil such that the antenna coil and the selected mapping electrode overlap relative to the longitudinal axis of the flexible tubular member. In certain preferred embodiments, the electrodes are ion implanted on the flexible tubular member such that the electrodes are flexible.

BRIEF DESCRIPTION OF THE DRAWINGS

The inventions, together with further objects and advantages thereof, may best be understood by reference to the following description taken in conjunction with the accompanying drawings in which:

FIG. 7b is a end view of the antenna coil of FIG. 7a.

FIG. 8 is a diagrammatic cross sectional side view of the distal end portion of an ablation catheter having a distally opening spirally wound conical antenna coil in accordance with another embodiment of the present invention.

FIG. 9 is a diagrammatic cross sectional side view of the distal end portion of an ablation catheter having a proximately opening spirally wound conical antenna coil in accordance with another embodiment of the present invention.

DESCRIPTION OF THE INVENTION

Figure 1:
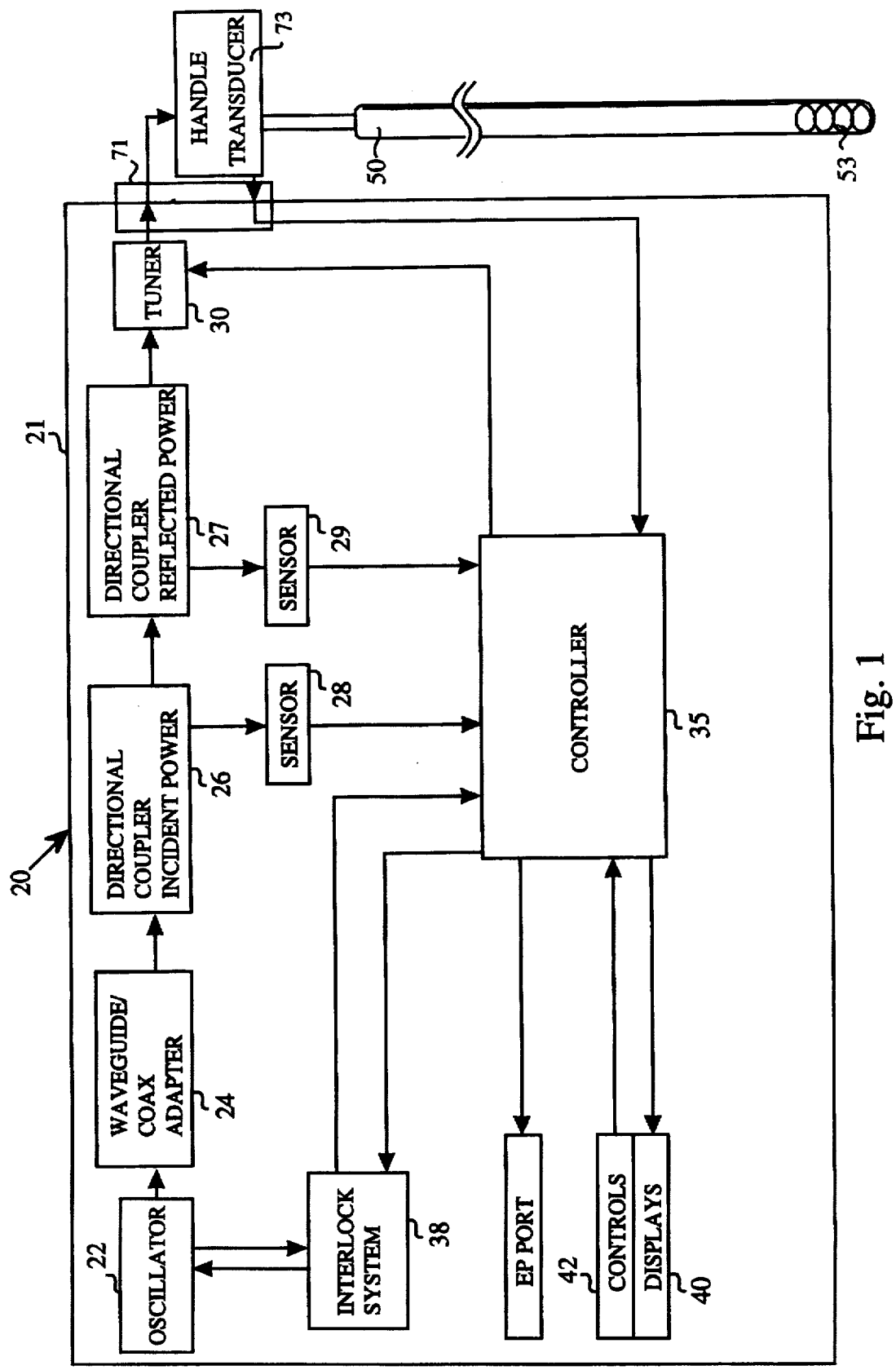
FIG. 1 is a diagrammatic illustration of a microwave ablation catheter system in accordance wit one embodiment of the present invention.
Figure 2:
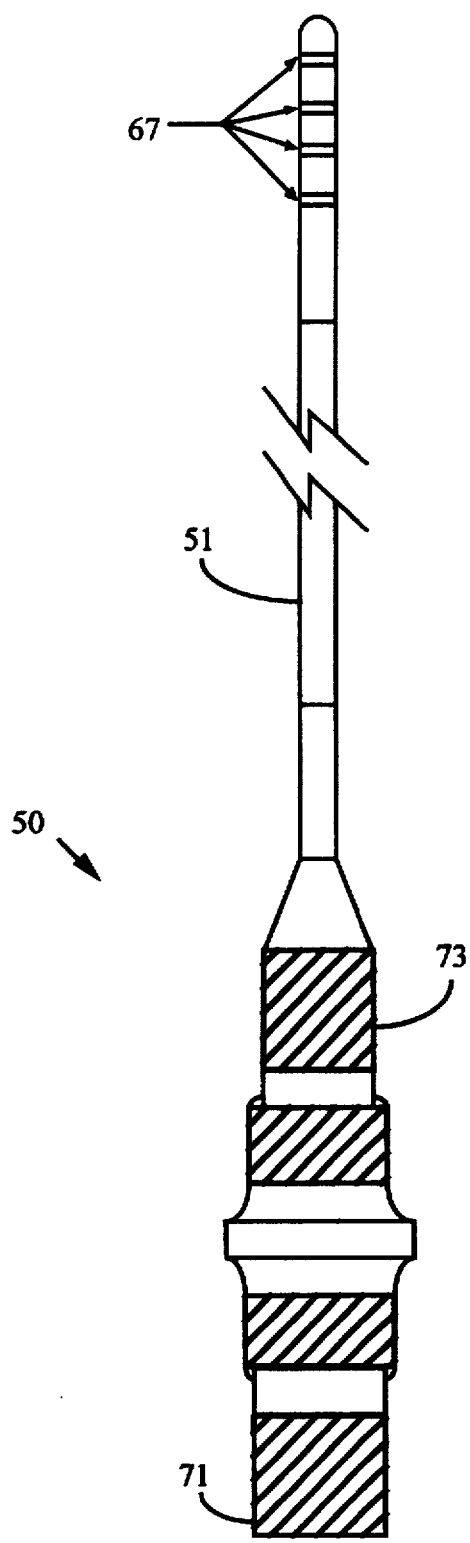
FIG. 2 is a diagrammatic illustration of the catheter shown in FIG. 1.
Figure 3:
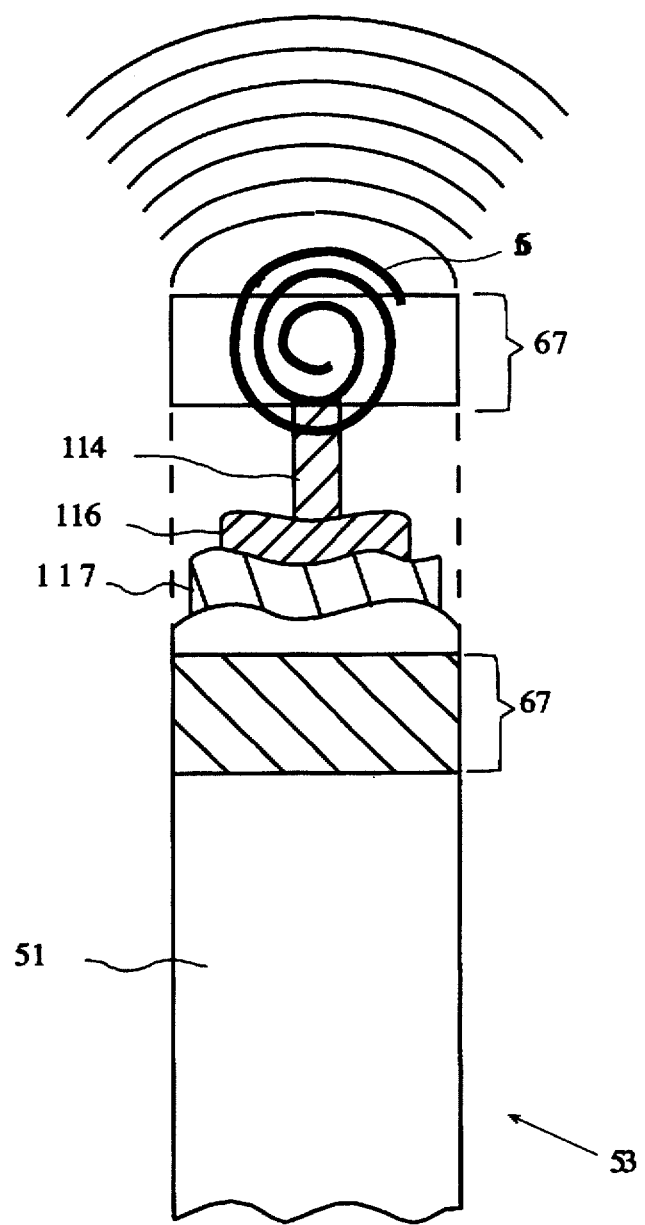
FIG. 3 is a diagrammatic partially broken away side view of the distal end portion of an ablation catheter having a laterally oriented antenna coil in accordance with one embodiment of the present invention.

Several presently preferred ablation catheter systems in accordance with the present invention will be described below making reference to the accompanying drawings. As seen in FIG. 1, an ablation catheter system 10 generally includes a power supply 20 which is designed to generate controlled electromagnetic energy, a catheter 50 which is designed for insertion into a vessel (such as a coronary vessel) in the body of a patient and a connector 71 for coupling the power supply 20 to the catheter 50. Referring next to FIGS. 2 and 3, the catheter 50 typically includes a flexible outer tubing 51, a coaxial microwave transmission line 53 that extends through the flexible tubing 51 and an antenna 56 coupled to the distal end of the coaxial transmission line. The connector 71 couples the transmission line 53 to the external power supply 20. A handle 73 may be provided for use by the surgeon to facilitate steering and potentially other control functions. Additionally, the catheter may include a variety of sensors for monitoring the patient during insertion, positioning and/or use of the catheter. By way of example, such sensors may include a plurality of mapping electrodes 67 and one or more thermocouple wires (not shown). The coaxial microwave transmission line 53 includes a center conductor 114, a shield 117 and a dielectric material 116 disposed between the center conductor and shield.

The present invention relates to antenna geometries and catheter construction for use in microwave ablation catheters that are capable of creating electric fields that have a significant component that extends in a region in front of the distal tip of the antenna. In most embodiments, the antenna is located near the distal tip of the catheter, and thus, in such embodiments, the generated fields include a significant component that extends in a region in front of the distal tip of the catheter. These are generally referred to herein as "end fire" antenna configurations. However, the invention also has application to more proximately positioned and/or moveable antenna configurations as well. Many of the described designs are arranged to direct a majority of the field in a generally longitudinal direction relative to the catheter axis. By this it is meant that a majority of the field strength is within 45 degrees of the longitudinal axis of the catheter.

Figure 4:
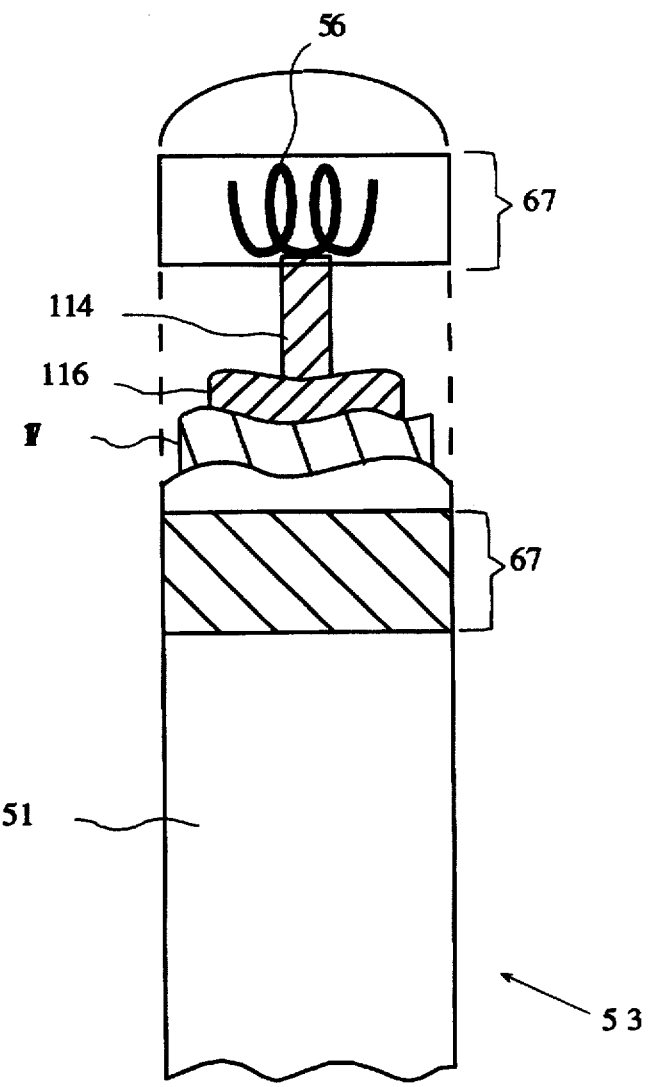
FIG. 4 is a diagrammatic top view of the distal end portion of the transmission line and antenna assembly of the ablation catheter shown in FIG. 3.

Referring next to FIGS. 3 and 4, an end fire antenna arrangement in accordance with one embodiment of the present invention will be described. In this embodiment, the antenna 56 is a helically wound antenna that is oriented perpendicularly relative to the coaxial cable. That is, the longitudinal axis of the antenna is perpendicular to the longitudinal axis of the catheter itself. This is referred to herein as a laterally oriented antenna coil arrangement. It is noted that the view in FIG. 3 is a schematic end view of an antenna having two and a half turns. Although the coils appear to spiral inward, this is simply to illustrate that the coil has a number of turns. As seen in the side view of the antenna 56 illustrated in FIG. 4, the diameter of the turns will typically remain constant along the length of the antenna, although this is not a requirement. The antenna may be formed from any suitable material. By way of example, silver plated copper and beryllium copper wires work well to form the antenna.

The antenna 56 is attached directly to the center conductor 114. The connection between the antenna 56 and center conductor 114 may be made in any suitable manner such as soldering, brazing, ultrasonic welding or adhesive bonding. By way of example in the described embodiment it is attached by soldering. In other embodiments, the antenna 56 can be wound from the transmission lines center conductor itself. This is more difficult from a manufacturing standpoint but has the advantage of forming a more rugged connection between the antenna and center conductor.

The actual number of turns of the antenna coil may vary a great deal in accordance with the needs of a particular system. Some of the factors that will dictate the number of turns used include the coil diameter and pitch, the catheter diameter, the desired field strength and the match within the heart tissue. By way of example, antenna coils having in the range of approximately 2 to 5 complete uninsulated turns work well. In embodiments where the turns are insulated, the pitch can be smaller and the number of turns increased.

The overall size of the antenna's may be widely varied, by way of examples, coil diameters in the range of approximately 1 to 2.5 mm that have a length in the range of approximately 1.5 to 3.0 mm work well in coronary applications. The antenna is typically spaced at least 0.5 mm, as for example in the range of approximately 0.5 to 2 mm, from the distal end of the transmission line shield 117 and at least approximately 0.5 mm, as for example in the range of approximately 0.5 to 1 mm from the distal end of the transmission line dielectric 116, as shown in FIGS. 3 and 4.

Figure 6:
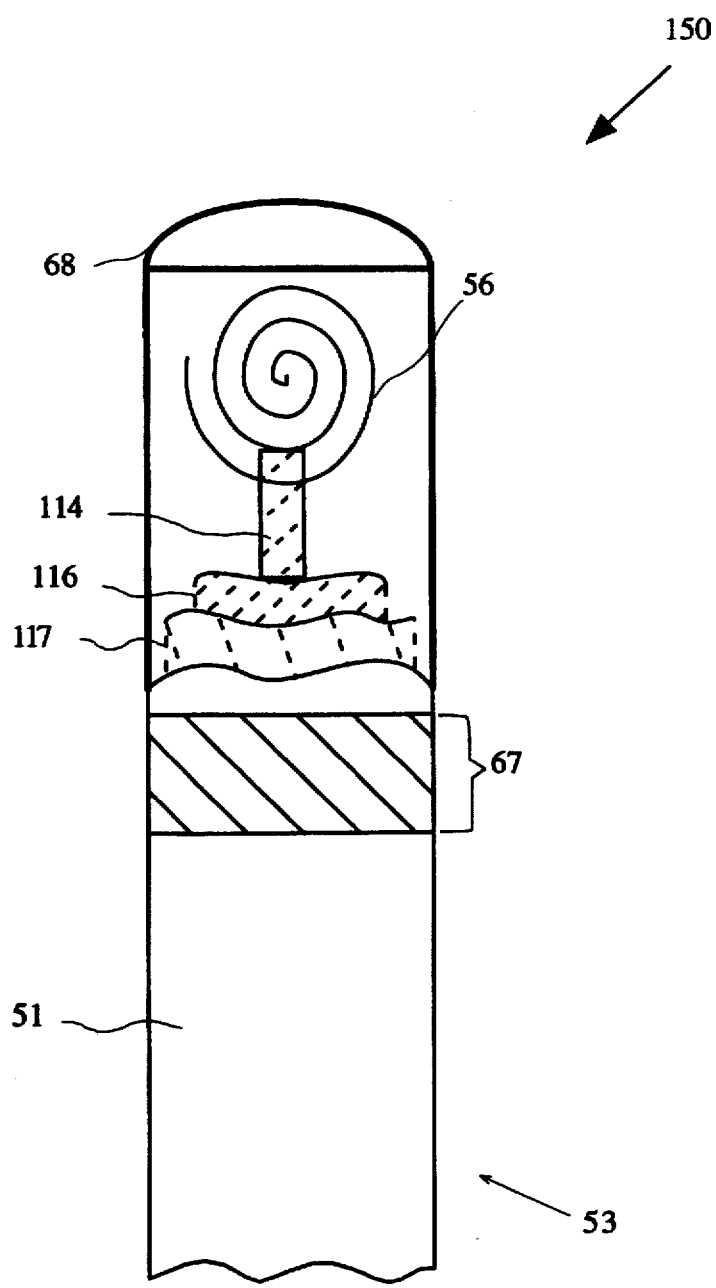
FIG. 6 is a diagrammatic partially broken away side view of the distal end portion of an ablation catheter having a distal electrode.

In one specific application, an antenna having in the range of two to four uninsulated turns, a coil diameter in the range of approximately 2 to 2.5 mm, and a length in the range of 1.8 to 2 mm has been found to work well. The described antenna was spaced approximately 1.5 mm, from the distal end of the transmission line shield 117 and approximately 0.5 mm from the distal end of the transmission line dielectric 116, as shown in FIGS. 3 and 4. Of course, these spacing dimensions may be varied widely to meet the requirements of a particular design. The termination of the transmission line shield may take any suitable form, such as a shield termination ring or other termination structure, soldering of the distal ends of the braided wires that make up the shield, simply as exposed braid wire ends. When a shield termination is used, it may be desirable to position the antenna coil at least 1 mm away The described lateral antenna coil arrangement is designed to provide a field pattern that maximizes the field strength in the region directly in front of the distal tip of the catheter as best illustrated in FIG. 3. The field is enhanced in a direction perpendicular to the axis of the coils, and thus, is stronger toward the tip in a generally forward direction. Therefore, with this arrangement it is best to take care to make sure that the distal tip of the catheter perpendicularly contacts the tissue to be ablated during surgical ablation. To facilitate positioning of the catheter during use, it is often desirable to provide one or more mapping stainless steel or iridium platinum electrodes 67 in the vicinity of the antenna. The mapping electrodes are used detect electrophysiological signals from the cardiac tissue and therefore can be used to map the relevant region of the heart prior to or after an ablation procedure. The electrodes may also be used to help position the catheter for use and monitor the patient's condition during the ablation process. In the embodiment shown in FIG. 3, lateral mapping electrodes include an electrode band that is positioned at substantially the same longitudinal position relative to the catheter as the antenna coil. In the embodiment shown in FIG. 6, a distal mapping electrode 68 is provided. Positioning the electrodes in these locations is believed to be particularly useful to facilitate mapping and monitoring. The mapping electrodes may be formed from any suitable material. By way of example, stainless steel and iridium platinum work well as the electrode materials.

It should be appreciated that catheters incorporating the described antenna arrangements may be fabricated in a variety of manners as will be apparent to catheter engineers familiar with the art. By way of example, one method of producing the antenna structure will now be described. In this embodiment, the antenna coil is formed from 0.010 inch diameter silver plated copper wire that is wound on a mandrel. The antenna coil is attached to the center conductor of the transmission line that has been cropped as described above. A drop of ultraviolet curable epoxy (UV epoxy), as for example, Dymax 198-M is then placed on the coil to hold its shape. The antenna coil is then placed in a first mold (which by way of example, may be a 0.084 inch diameter pin gauge mold) and UV epoxy is filled in the mold to form an antenna cap. Excess epoxy can then be removed using a scalpel. A thermocouple wire (not shown) may then be coupled to the assembly using a heat shrink tubing 84 that is secured by epoxy. The catheter tip is then trimmed to a distance that is half a millimeter from the distal end of the antenna. It is noted that with this arrangement, the antenna is insulated from the surrounding tissue, which substantially eliminates the risks of charring that are inherent with exposed transducer designs.

A mapping electrode ring assembly having the desired number of electrode wires (not shown), such as a pair of electrode wires, may then be slid over the antenna assembly and positioned in its desired location. The tip assembly is then placed in a second mold (which by way of example may be a 0.094 inch diameter pin gauge mold). The second mold is then filed with UV epoxy and cured to set the electrodes. A grinder may then be used to slice cuts in the electrode ring assembly to electrically isolate a pair of electrodes. The 0.094 inch diameter mold may then be used to fill in the slots formed by the cuts using more UV epoxy. After the epoxy has cured, any excess material may be trimmed and the transmission line/antenna assembly is completed. As will be appreciated by those skilled in the art, the assembly may then be inserted into a flexible tubular member in a conventional manner. Of course, stiffening wires, steering wires, additional sensor wires, etc., may all be included in the final assembly as required by a particular design. In one embodiment an E-type thermocouple is placed 0.5 mm–1 mm back from the shield.

Figure 5:
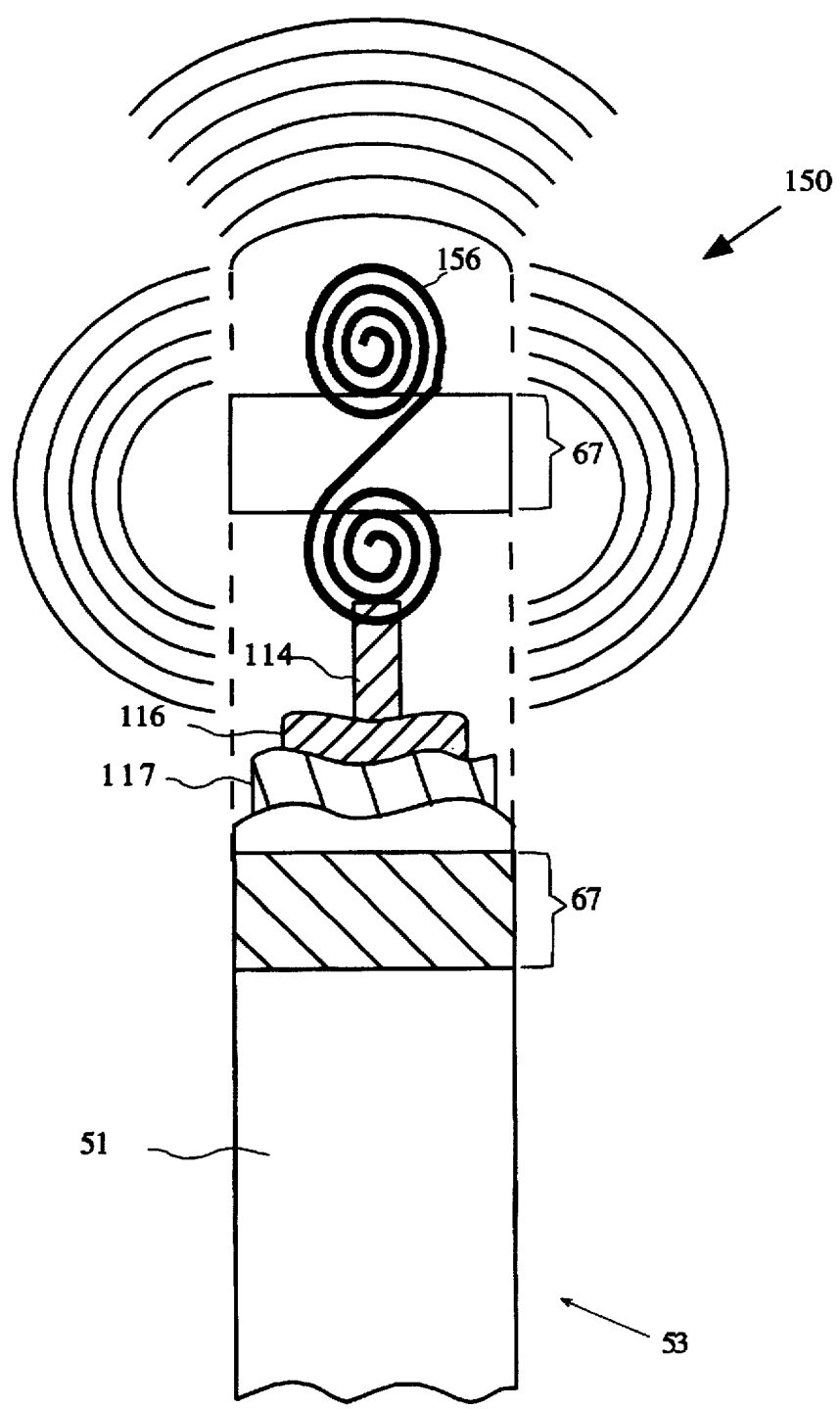
FIG. 5 is a diagrammatic partially broken away side view of the distal end portion of a transmission line and antenna assembly of an ablation catheter having a pair of laterally oriented antenna coil in accordance with another embodiment of the present invention.

One feature of the lateral coil antenna structure described above is that the field is strongest in a region directly in front of the catheter tip. In many applications this is desirable. However, in some applications it may be difficult to insure that the catheter perpendicularly contacts the region to be ablated. If perpendicular contact can not be achieved, the lesion size will typically be relatively small. Referring next to FIG. 5, an alternative antenna arrangement 150 that is capable of providing larger lesions in the event that perpendicular contact can not be assured will be described. In this embodiment, a pair of laterally arranged antenna coils 156 are provided that are spaced apart longitudinally relative to the catheter axis. The size and geometry of the coils 156 may be similar to the geometry of those described above with reference to the single laterally arranged antenna coil embodiment. The double coil antenna structure 150 has the advantage of extending further along the longitudinal axis of the catheter than the single laterally arranged antenna coil construction. By way of example, in the described embodiment, the antenna structure 150 has an overall length in the range of approximately 3 to 5 mm as for example, 3.5 mm. This additional length is advantageous when the catheter does not perpendicularly contact the tissue to be ablated. As can be seen in the illustration the field generated by this type of antenna structure tends to have a significant lateral component in addition to a significant distal component.

The double coil structure may be formed from a single wire that is attached to the center conductor 114, or may be formed from the center conductor 114 of transmission line 53 as described above. Alternatively, the antenna coils 156 may be separately formed and coupled by a suitable electrically conductive bond or jumper wire. A catheter incorporating the double coil antenna structure may be formed in a manner similar to the method described above with reference to the single lateral coil antenna structure 56. The spacings described above between the shield and the single laterally arranged antenna coil are suitable for the double coil antenna structure as well It should also be apparent that in some applications it may be desirable to provide additional laterally arranged antenna coils.

Figure 7B:
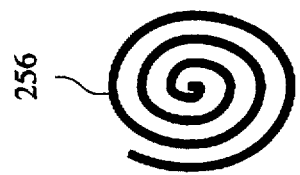
Figure 7A:
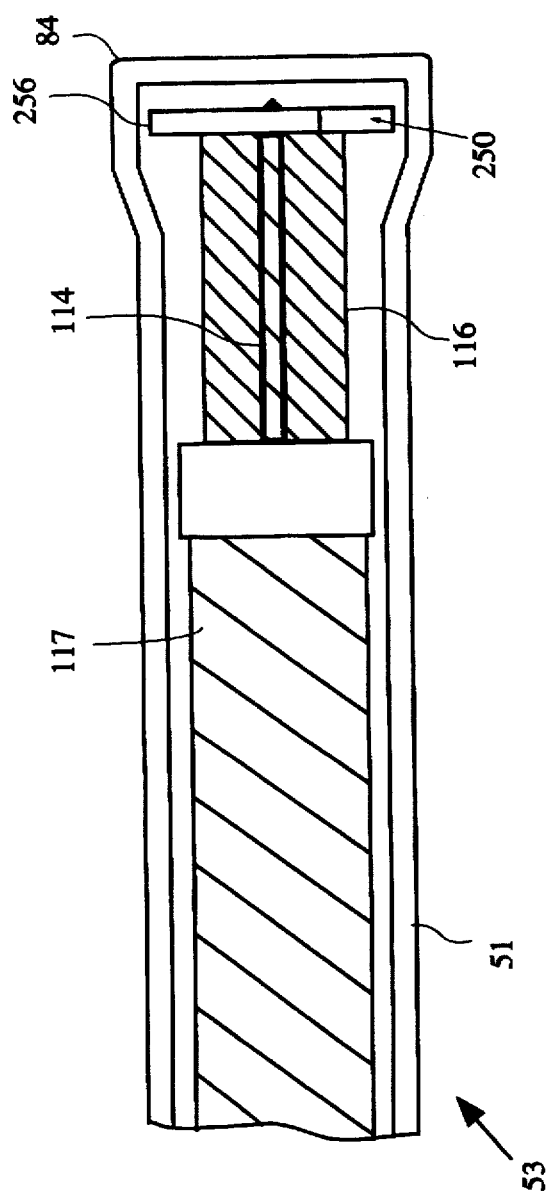
FIG. 7a is a diagrammatic cross sectional side view of the distal end portion of an ablation catheter having a flat spirally wound antenna coil in accordance with another embodiment of the present invention.

Referring next to FIGS. 7(a) and 7(b), another end fire antenna construction 250 will be described. In this embodiment, the coil 256 is spirally wound in a flat coil which is coupled to the distal end of the co-axial transmission line center conductor 114. As in the previous described embodiments, the antenna coil 256 may be attached to the center conductor by any suitable process such as soldering. Alternatively, the coil may formed from the center conductor itself. Like the first described embodiment, the flat spiral coil arrangement creates a field that extends most prominently in a longitudinal direction relative to the catheter. This can be very useful when it is necessary to perform ablation of larger tissue volumes.

In other embodiments, it may be desirable to create a field that is most prominent in a direction that extends at a forward angle relative to the catheter tip. A few spirally wound antenna geometries that are well suited for such application will now be described with reference to FIGS. 8 and 9. In the embodiment shown in FIG. 8, a cone shaped spiral antenna arrangement that expands in a distal direction is illustrated. In the embodiment shown in FIG. 9, a cone shaped spiral antenna arrangement that expands in the proximal direction is illustrated. In alternative embodiments, the coils may be wound in a frustoconical manner. The slope of the cone face may be varied widely in accordance with the needs of a particular application. By way of example, cone face slope angles in the range of approximately 30 to 90 degrees have been found to work well. (With a 90 degree being a flat spiral as described above). Of course, the slope of the antenna coil face will have a direct bearing on the field pattern created during use of the catheter, with smaller cone face slope angles providing wider lesions and steeper angles providing narrower and generally deeper lesions. These conical and frusto-conical spiral shaped antennas may either be attached to or formed from the center conductor of the transmission line.

The spiral shaped antenna coils may be formed by winding a wire in a flat coil. The actual external diameter of the coil may be varied in accordance with the needs of a particular system. By way of example in coronary ablation catheters coil diameters in the range of approximately 2 to 2.5 mm as for example approximately 0.100 inches in diameter may be used. The coiled antenna may then be attached to the distal tip of the center conductor 1 14. If a conical coil is to be formed, a flat coil may be stretched into a conical shape using a pin with the appropriate face angle.

Figures 10A, 10B:
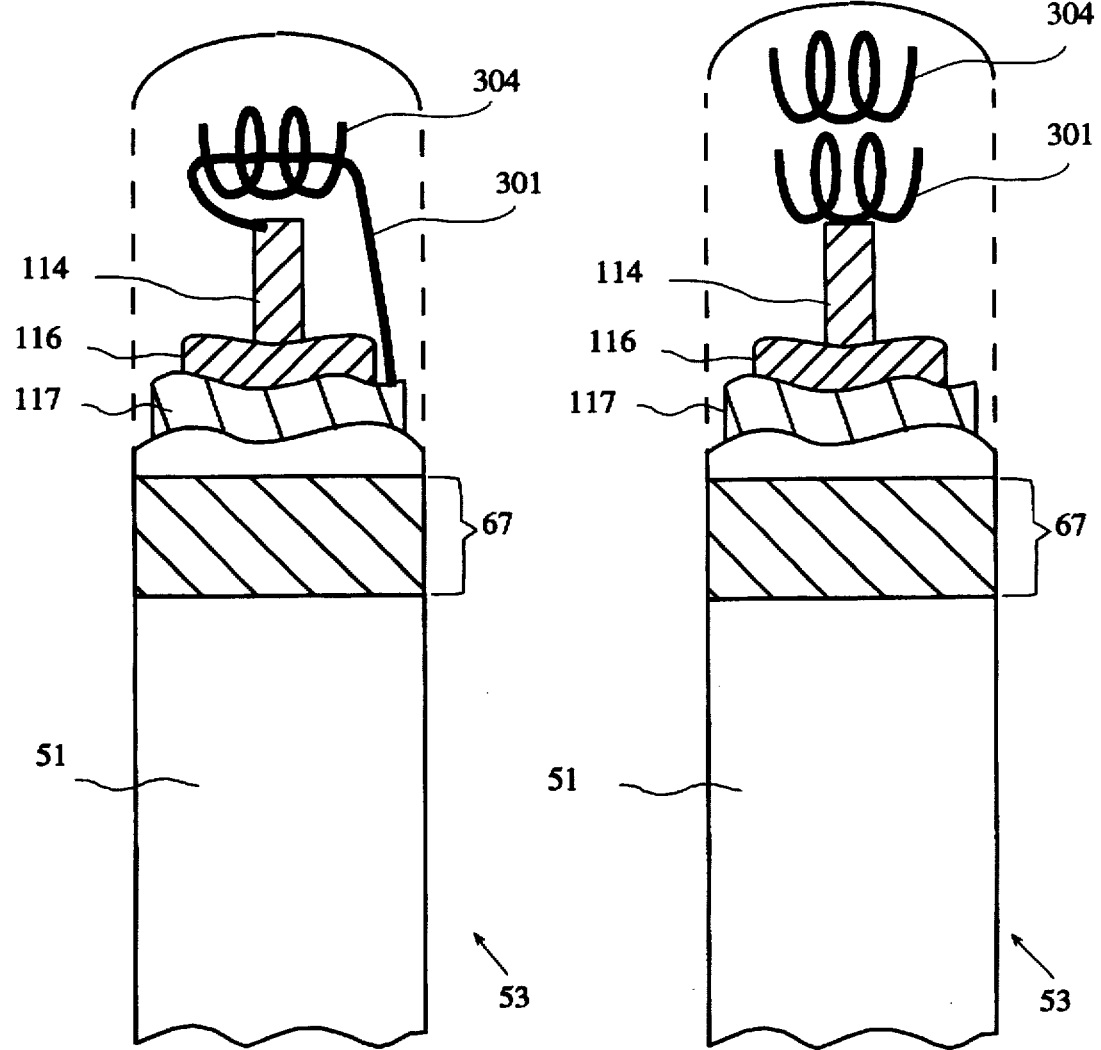
FIG. 10(a) and 10(b) are diagrammatic cross sectional side views of the distal end portions of two ablation catheter embodiments having antenna structures that utilizes a transformer effect.

Referring next to FIG. 10(a), another embodiment of the invention will be described. In this embodiment, a primary coil 301 is formed by a wire that connects the center conductor 114 of the transmission line 53 to the transmission line shield 117. A laterally extending secondary coil 304 then serves as the antenna. The primary and secondary coils do not contact one another and therefor act as a transformer. In Figure 10(a), the primary coil 301 passes through the center of the secondary coil 304, but does not physically contact the secondary coil. As will be appreciated by those skilled in the art, the relative positioning of the primary and secondary coils may be widely varied will still obtaining the desired transformer affect. By way of example, FIG. 10(b) illustrates an embodiment wherein the secondary coil 304 is positioned distally of the primary coil 301.

The desired forward firing effect can also be accomplished using more complicated antenna winding techniques such as stepped windings and coils structures that double back upon themselves. Additionally, a forward firing effect can be created using an insulated spherical antenna or a cylindrical antenna that is open on its proximal end but closed on its distal end. In such embodiments, the antenna structure is coupled to the center conductor a spaced distance from the shield termination 95. The spacing may optionally be accomplished using the co-axial cable dielectric or a Teflon insulator plug. The antenna structure is then encased with a dielectric cap that may be formed from any suitable material such as Teflon. The cap would typically extend back over the shield termination.

Figure 11:
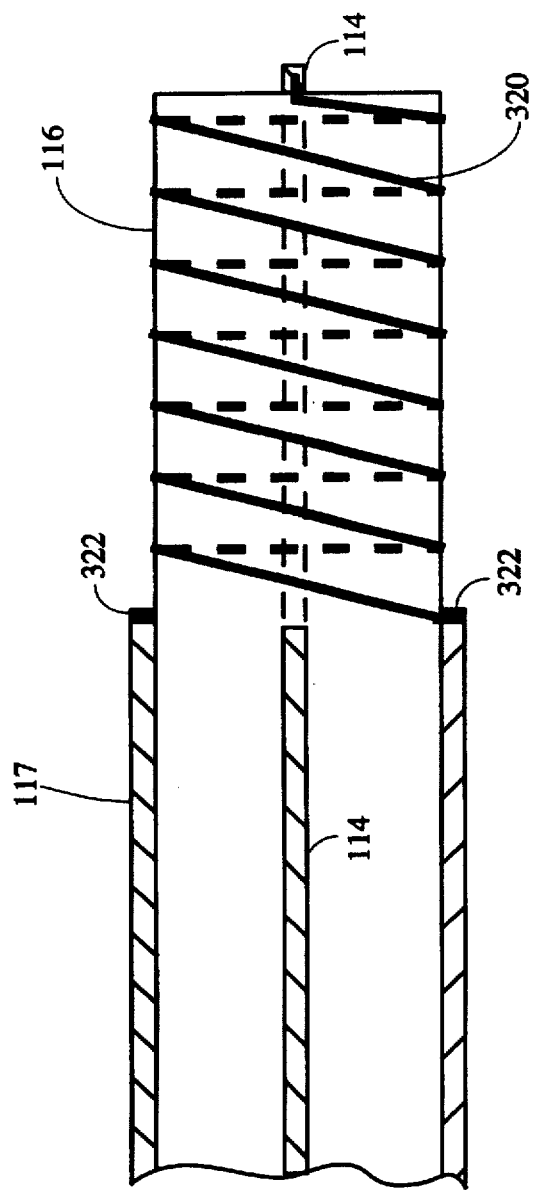
FIG. 11 is a diagrammatic cross sectional side view of the distal end portion of a transmission line and antenna structure having a longitudinally extending antenna that is grounded to the shield of the coaxial cable.

Referring next to FIG. 11 a very different antenna structure will be described. In this embodiment, a longitudinally extending helical coil 320 is provided. The orientation of the helical coil is similar to conventional helical antenna designs. However, unlike conventional coil based microwave antennas, the coil is coupled between the center conductor 114 and the shield 117 of transmission line 53. This is contrasted with conventional arrangements which are typically only electrically connected to the center conductor. In the embodiment shown, the center conductor 114 and dielectric 116 extend beyond the termination of the shield 117. The distal tip of the coil 320 is attached to the distal tip of the center conductor 114. The coil 320 is wound about the distal end of the dielectric and the proximal end to the coil 320 is electrically coupled to the distal end of the shield 117. In the embodiment shown, the coil 320 is coupled to shield termination 322. However, in other embodiments, the shield termination may be eliminated and the coil 320 may be directly coupled to the shield 117.

The described grounding of the antenna serves to better define the electromagnetic field generated during use. Specifically, when a longitudinally extending coil is used, the field extends substantially perpendicularly to the antenna and is fairly well constrained to the length of the antenna itself regardless of the power used. This arrangement serves to provide better control during ablation. Thus, catheters having specified ablation characteristics can be fabricated by building catheters with different length antennas.

The length, pitch and coil diameter of the grounded antenna coil 320 may be widely varied in accordance with the needs of a particular application. The antennas in any of the described embodiments may be formed from any suitable material such as copper, silver or gold wire, plated wires such as silver plated copper, and the like. Alternatively, the antennas can be wound from the center conductor 114 of the transmission line.

Referring next to FIG. 1, a power supply 20 suitable for powering the microwave ablation catheter will be briefly described. However, it should be appreciated that the nature and design of the power supply may be widely varied and its design is not particularly important to the present invention. In the embodiment shown, the power supply 20 includes a casing 21 having a microwave generator 22, a waveguide adapter 24, a pair of directional couples 27 & 28 that interface with power monitors 121, a tuner 30, a controller and an interlock system 38 all enclosed therein. The front panel 39 of the casing has various displays 40 and controls 42, as well as a port 43 to which conventional EP signal monitoring equipment can be coupled. The electrode wires would typically be in electrical communication with this EP signal monitoring equipment.

The microwave generator 22 may take any conventional form. When using microwave energy for tissue ablation, the optimal frequencies are generally in the neighborhood of the optimal frequency for heating water. By way of example, frequencies in the range of approximately 800 MHz to 6 GHz work well. At the time of this writing, the frequencies that are approved by the U.S. Food and Drug Administration for experimental clinical work are 915 MHz and 2.45 GHz. Therefore, a power supply having the capacity to generate microwave energy at frequencies in the neighborhood of 2.45 GHz may be chosen. At the time of this writing, solid state microwave generators in the 1–3 GHz range are very expensive. Therefore, a conventional magnetron of the type commonly used in microwave ovens is utilized as the generator. It should be appreciated, however, that any other suitable microwave power source could be substituted in its place.

The microwave energy is transmitted from the microwave generator 22 through a waveguide and coax adapter 24 to a pair of directional couplers 27, 28 used to monitor forward and reflected power respectively. The output of each directional coupler is connected to an associated power sensor 121. These output signals are indicative of the forward and reflected power to the controller. It is contemplated that other suitable power monitors could be used in place of the described directional coupler/power sensor arrangements. Following the directional couplers, the transmission line may be equipped with a tuner mechanism 30 that is controlled by the controller 35 to facilitate impedance matching throughout the catheter system. In alternative embodiments, a tuning mechanism may be provided in the catheter as described in U.S. Pat. No. 5,405,346. Downstream from the tuner 30, the power is directed through a quick disconnect jack and plug (connector 71) to the catheter 50 itself. System controls are provided for operation of the power supply as is a display for displaying such information as system set points, forward and reflected power, temperatures, etc. The controller 35 may take the form of dedicated logic, but in a preferred embodiment a conventional microprocessor or computer is used.

As will also be appreciated by those skilled in the art, the catheter 50 may be constructed in a wide variety of manners without departing from the spirit or scope of the invention By way of example, the outer flexible tubing member 51 may take any suitable form. The embodiment shown includes an elongated tube portion 54 and a distal cap or plug 63 that protects the antenna. The tube portion 54 is arranged to receive a number of components. It may include an enlarged lumen for the coaxial transmission line and a plurality of smaller lumens for the various other wires such a sensory wires (such as electrode wires and thermometry wires), steering wires and/or stiffening wires. Alternatively, all of the wiring may pass through a single lumen, or a combination approach may be used. As will be appreciated by those skilled in the art, the arrangement and number of lumens actually used may be widely varied in accordance with the needs of a particular catheter.

The outer tubing 51 may be made of any suitable material such as medical grade polyolefins, fluoropolymers, or polyvinylidene fluoride. By way of example, PEBAX resins from Autochem of Germany have been used with success for the outer tubing of the body of the catheter. However, epoxy and Teflon type products are generally preferred for the region of the distal cap since they are better suited for handling the high thermal stresses that occur in the vicinity of the antenna during ablation.

As will be appreciated by those skilled in the art, in coronary applications, the catheter diameter is typically limited to approximately 7 ½ French (approximately 2.5 mm in diameter). In microwave ablation catheter systems it is important to use a coaxial transmission line that is not too small in diameter to insure that the attenuation within the catheter is not to large. By way of example, coaxial transmission lines that are on the order of 72 mils in diameter (1.8 mm) tend to work well in microwave ablation catheter systems.

In some embodiments, the catheter 50 may also include a series of mapping electrodes bands 67 near the tip of the catheter to detect electrophysiological signals from the cardiac tissue. Such electrodes can be used to map the relevant region of the heart prior to or after an ablation procedure. The electrodes may also be used to monitor the patient's condition during the ablation process. The electrode bands may optionally be divided into a plurality of electrically isolated electrode segments. The information obtained from the electrodes is transmitted via electrode wires (not shown), through connector 70 and through the power supply 20 to external electronics such as an EP signal monitoring device. Filtering of the signal may be provided as necessary. In alternative embodiments, some of the external electronics could be incorporated into the power supply and/or the power supply could use information obtained from the electrodes in its control scheme. Additionally, one or more distal electrodes 57 may optionally be provided at the distal tip of the catheter in the antenna region. In some embodiments, the electrode material is directly ion implanted on the flexible tubular member. One significant advantage of the ion implantation approach is that the arcuate electrodes themselves are essentially as flexible as the tubular member and thus do not inhibit the catheter's maneuverability regardless of the electrode dimensions. This even further improves the maneuverability of the catheter tip and permits the use of electrodes of any desired size since it is relatively easy to control the electrode dimensions in the ion implantation process. By way of example, a variety of suitable mapping electrode arrangements are described in detail in co-pending application Ser. No. 08/497,941 filed Jun. 30, 1995 which is incorporated herein by reference in its entirety.

One method for using the described catheter in a coronary ablation procedure will now be described. The catheter may be fed through the femoral artery or other suitable vessel and into the appropriate region of the heart. By way of example, to treat ventricular tachycardia, the catheter tip is typically fed into the appropriate ventricle chamber. With the catheter properly positioned, the electrodes can detect electrical signals in the adjacent regions of the heart. Thus, the various electrodes are monitored to effectively "map" the region of the heart of interest. If necessary, the catheter can be further inserted, and or withdrawn to further facilitate mapping the region of interest. Typically, the mapping will indicate the location at which desired signal are the strongest, which will permit the physician to determine the appropriate ablation position. The catheter is then withdrawn or further inserted as necessary to position the antenna properly for the ablating procedure. After the antenna is properly positioned, microwave energy is applied to the co-axial transmission line to facilitate the ablation. During the ablation procedure, as well as after the operation is completed, the electrodes may be used to monitor the ablation process as well as the results.

Although only a few embodiments of the present inventions have been described in detail, it should be understood that the present inventions may be embodied in many other specific forms without departing from the spirit or scope of the inventions. Particularly, the invention has been described in terms of a microwave ablation catheter for cardiac applications, however, it should be appreciated that the described small diameter microwave ablation catheter could be used for a wide variety of non-cardiac ablation applications as well. The size and pitch of the described antenna coils may be widely varied. It should also be appreciated that the laterally oriented antenna coil does not need to be strictly perpendicular relative to the catheter axis and indeed, in some embodiments it may be desirable to tilt the antenna coil somewhat.

In one described configuration, a longitudinally extending coil is grounded to the shield which provides significantly better control of the field. The grounding of the coil may prove effective in other geometries as well.

It is contemplated that both the catheter design and the design of the power supply may be widely modified without departing from the scope of this invention. Therefore, the present examples are to be considered as illustrative and not restrictive, and the invention is not to be limited to the details given herein, but may be modified within the scope of the appended claims.

We claim:

1. A microwave ablation catheter comprising:

an elongated flexible tubular member adapted to be inserted into a vessel in the body of a patient, the flexible tubular member including a distal portion, a proximal portion and a longitudinal catheter axis;

a coaxial transmission line disposed within the tubular member, the transmission line having proximal and distal ends and being suitable for transmission of microwave energy at frequencies in the range of approximately 800 to 6000 megahertz;

a connector suitable for coupling the proximal end of the transmission line to a microwave energy source;

an antenna coupled to the transmission line for generating an electric field sufficiently strong to cause tissue ablation, the antenna geometry being arranged to direct a majority of the field in a generally longitudinal direction relative to the catheter axis.

2. A catheter comprising:

an elongated flexible tubular member adapted to be inserted into a vessel in the body of a patient, the flexible tubular member including a distal portion and a proximal portion and a longitudinal axis;

a transmission line disposed within the tubular member, the transmission line having proximal and distal ends, wherein the proximal end of the transmission line is suitable for connection to an electromagnetic energy source;

a connector suitable for coupling the proximal end of the transmission line to an electromagnetic energy source;

an antenna coil coupled to the transmission line for generating an electric field sufficiently strong to cause tissue ablation, the antenna coil having a longitudinal axis that extends substantially perpendicular to the longitudinal axis of the flexible tubular member.

3. A catheter as recited in claim 2 wherein:

the transmission line is a coaxial transmission line suitable for transmission of microwave energy at frequencies in the range of approximately 800 to 6000 megahertz, the coaxial transmission line having a center conductor, a shield and a dielectric material disposed between the center conductor and shield; and the antenna coil is coupled to the center conductor of the coaxial transmission line.

4. A catheter as recited in claim 3 wherein a middle portion of the antenna coil is coupled directly to the center conductor, and the antenna coil has at least two full turns.

5. A catheter as recited in claim 2 wherein the antenna coil has at least two full turns.

6. A catheter as recited in claim 2 wherein the antenna coil has in the range of two to four full turns.

7. A catheter as recited in claim 2 wherein the antenna coil has a diameter in the range of approximately 1 to 2.5 millimeters.

8. A catheter as recited in claim 7 wherein the antenna coil has a length in the range of approximately 1.5 to 3 millimeters.

9. A catheter as recited in claim 2 further comprising a plurality of the antenna coils, the longitudinal axes of the antenna coils being spaced apart relative to the longitudinal axis of the flexible tubular member.

10. A catheter as recited in claim 9 wherein the plurality of the antenna coils are formed from a single wire.

11. A microwave ablation catheter comprising:

an elongated flexible tubular member adapted to be inserted into a vessel in the body of a patient, the flexible tubular member including a distal portion and a proximal portion and a longitudinal axis;

a coaxial transmission line disposed within the tubular member, the coaxial transmission line having a center conductor, a shield, a dielectric material disposed between the center conductor and shield, and proximal and distal ends;

a connector suitable for coupling the proximal end of the coaxial transmission line to a microwave energy source;

a substantially helical antenna coil having at least two full turns, the antenna coil being coupled the distal end of the center conductor of the coaxial transmission line for generating an electric field sufficiently strong to cause tissue ablation, the antenna coil having a longitudinal axis that extends substantially perpendicular to the longitudinal axis of the flexible tubular member.

12. A microwave ablation catheter as recited in claim 11 wherein the antenna coil has a diameter in the range of approximately 1 to 2.5 millimeters and a length in the range of approximately 1.5 to 3.0 millimeters.

13. A microwave ablation catheter as recited in claim 11 further comprising a shield termination coupled to the distal end of the coaxial transmission line shield and wherein the antenna coil is positioned at least 1 mm away from the shield termination.

14. A microwave ablation catheter as recited in claim 11 wherein the antenna coil is positioned distally of the distal end of the coaxial transmission line shield in the range of approximately 0.5 to 2 mm from the shield.

15. A microwave ablation catheter as recited in claim 14 wherein the antenna coil is positioned distally of the distal end of the coaxial transmission line dielectric in the range of approximately 0.5 to 1 mm from the dielectric.

16. A microwave ablation catheter as recited in claim 11 further comprising a plurality of the antenna coils, the longitudinal axes of the antenna coils being spaced apart relative to the longitudinal axis of the flexible tubular member.

17. A microwave ablation catheter as recited in claim 16 wherein the plurality of the antenna coils are formed from a single wire.

18. A microwave ablation catheter as recited in claim 11 wherein the antenna coil is formed from the center conductor of the coaxial transmission line.

19. A microwave ablation catheter as recited in claim 11 further comprising a lateral mapping electrode positioned adjacent the antenna coil such that antenna coil and the mapping electrode overlap relative to the longitudinal axis of the flexible tubular member.

20. A microwave ablation catheter as recited in claim 11 further comprising a lateral mapping electrode band positioned adjacent the antenna coil such that antenna coil and the mapping electrode band overlap relative to the longitudinal axis of the flexible tubular member, the mapping electrode band including a plurality of electrically isolated electrodes.

21. A catheter as recited in claim 20 wherein the electrodes are ion implanted on the flexible tubular member such that the electrodes are flexible.

22. A catheter comprising:

an elongated flexible tubular member adapted to be inserted into a vessel in the body of a patient, the flexible tubular member including a distal portion and a proximal portion and a longitudinal axis;

a transmission line disposed within the tubular member, the transmission line having proximal and distal ends, wherein the proximal end of the transmission line is suitable for connection to an electromagnetic energy source;

a connector suitable for coupling the proximal end of the transmission line to an electromagnetic energy source;

an antenna coil coupled to the transmission line for generating an electric field sufficiently strong to cause tissue ablation, wherein at least a portion of the antenna coil is spirally wound in one selected from the group consisting of a descending spiral and are ascending spiral, and wherein the diameter of the antenna coil increases or decreases in the direction from a proximal to distal end of the antenna thereby forming a descending or ascending spiral.

23. A catheter comprising:

an elongated flexible tubular member adapted to be inserted into a vessel in the body of a patient, the flexible tubular member including a distal portion and a proximal portion and a longitudinal axis;

a transmission line disposed within the tubular member, the transmission line having proximal and distal ends, wherein the proximal end of the transmission line is suitable for connection to an electromagnetic energy source, a connector suitable for coupling the proximal end of the transmission line to an electromagnetic energy source;

an antenna coil coupled to the transmission line for generating an electric field sufficiently strong to cause tissue ablation, wherein at least a portion of the antenna coil is wound in a substantially flat spirally wound coil, the antenna coil being spirally wound in one selected from the group consisting of a descending spiral wherein the diameter of the antenna coil decreases with adjacent turns and an ascending spiral wherein the diameter of the antenna coil increases with adjacent turns.

24. A catheter as recited in claim 22 wherein the antenna coil is wound in a substantially conical or frusto-conical coil.

25. A catheter as recited in claim 24 wherein the antenna coil expands distally such that a distal end of the antenna coil has a larger diameter than a proximal end of the antenna coil.

26. A catheter as recited in claim 24 wherein the antenna coil contracts distally such that a distal end of the antenna coil has a smaller diameter than a proximal end of the antenna coil.

27. A microwave ablation catheter comprising:

an elongated flexible tubular member adapted to be inserted into a vessel in the body of a patient, the flexible tubular member including a distal portion and a proximal portion and a longitudinal axis;

a coaxial transmission line disposed within the tubular member, the coaxial transmission line having a center conductor, a shield, a dielectric material disposed between the center conductor and shield, and proximal and distal ends;

a connector suitable for coupling the proximal end of the coaxial transmission line to a microwave energy source;

a substantially spirally wound antenna coil having at least two full ascending or descending turns wherein the diameter of the antenna coil increases or decreases with adjacent turns the antenna coil being coupled to the distal end of the center conductor of the coaxial transmission line for generating an electric field sufficiently strong to cause tissue ablation.

28. A microwave ablation catheter as recited in claim 27 wherein the antenna coil is substantially conical in shape.

29. A microwave ablation catheter as recited in claim 27 wherein the antenna coil is substantially frusto-conical in shape.

30. A microwave ablation catheter as recited in claim 27 wherein the antenna coil is substantially conical or frusto-conical in shape and a distal end of the antenna coil has a larger diameter than a proximal end of the antenna coil.

31. A microwave ablation catheter as recited in claim 27 wherein the antenna coil is substantially conical or frusto-conical in shape and a distal end of the antenna coil has a smaller diameter than a proximal end of the antenna coil.

32. A microwave ablation catheter as recited in claim 27 wherein the antenna coil is formed from the center conductor of the coaxial transmission line.

33. A microwave ablation catheter as recited in claim 27 further comprising a lateral mapping electrode positioned adjacent the antenna coil such that antenna coil and the mapping electrode overlap relative to the longitudinal axis of the flexible tubular member.

34. A microwave ablation catheter as recited in claim 27 wherein the antenna coil is wound in a substantially flat coil.

* * * * *